(12) United States Patent
Guynn

(10) Patent No.: US 11,839,593 B2
(45) Date of Patent: *Dec. 12, 2023

(54) PENETRATING TOPICAL PAIN RELIEF COMPOSITIONS AND METHODS OF USE

(71) Applicant: Tech Swerve LLC, Salt Lake City, UT (US)

(72) Inventor: John M. Guynn, Salt Lake City, UT (US)

(73) Assignee: TECH SWERVE LLC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/196,889

(22) Filed: May 12, 2023

(65) Prior Publication Data

US 2023/0301935 A1  Sep. 28, 2023

Related U.S. Application Data

(63) Continuation of application No. 17/884,918, filed on Aug. 10, 2022, which is a continuation-in-part of application No. 17/408,316, filed on Aug. 20, 2021, now Pat. No. 11,446,278, which is a continuation-in-part of application No. PCT/US2020/034984, filed on May 28, 2020.

(60) Provisional application No. 63/015,652, filed on Apr. 26, 2020, provisional application No. 62/853,710, filed on May 28, 2019.

(51) Int. Cl.
| | |
|---|---|
| *A61K 31/05* | (2006.01) |
| *A61K 31/01* | (2006.01) |
| *A61P 29/00* | (2006.01) |
| *A61K 31/352* | (2006.01) |
| *A61K 47/20* | (2006.01) |
| *A61K 47/10* | (2017.01) |
| *A61K 9/107* | (2006.01) |
| *A61K 9/06* | (2006.01) |
| *A61K 47/14* | (2017.01) |
| *A61K 47/44* | (2017.01) |
| *A61K 47/12* | (2006.01) |
| *A61K 47/46* | (2006.01) |
| *A61K 31/045* | (2006.01) |
| *A61K 31/015* | (2006.01) |
| *A61K 9/00* | (2006.01) |

(52) U.S. Cl.
CPC ............ *A61K 31/05* (2013.01); *A61K 9/0014* (2013.01); *A61K 9/06* (2013.01); *A61K 9/107* (2013.01); *A61K 31/01* (2013.01); *A61K 31/015* (2013.01); *A61K 31/045* (2013.01); *A61K 31/352* (2013.01); *A61K 47/10* (2013.01); *A61K 47/12* (2013.01); *A61K 47/14* (2013.01); *A61K 47/20* (2013.01); *A61K 47/44* (2013.01); *A61K 47/46* (2013.01); *A61P 29/00* (2018.01)

(58) Field of Classification Search
CPC ....................................................... A61K 31/05
See application file for complete search history.

(56) References Cited

U.S. PATENT DOCUMENTS

| | | | |
|---|---|---|---|
| 9,533,942 B2 * | 1/2017 | Stinchcomb | .......... C07C 219/16 |
| 10,278,951 B1 * | 5/2019 | Newland | .............. A61K 9/0053 |
| 10,383,816 B2 | 8/2019 | Aung-Din | |
| 17,884,918 * | 8/2022 | Guynn | .................... A61K 31/05 |
| 11,446,278 B2 * | 9/2022 | Guynn | .................... A61P 29/02 |
| 2009/0247619 A1 * | 10/2009 | Stinchcomb | ........... A61K 47/32 |
| | | | 514/733 |
| 2010/0273895 A1 | 10/2010 | Stinchcomb et al. | |
| 2011/0052694 A1 | 3/2011 | Stinchcomb et al. | |
| 2012/0202891 A1 | 8/2012 | Stinchcomb et al. | |
| 2012/0202892 A1 | 8/2012 | Stinchcomb et al. | |
| 2012/0264818 A1 * | 10/2012 | Newland | ................. A61P 31/04 |
| | | | 549/390 |
| 2013/0274321 A1 * | 10/2013 | Newland | .............. A61K 31/353 |
| | | | 514/454 |
| 2016/0256411 A1 * | 9/2016 | Aung-Din | ............... A61P 25/28 |
| 2017/0021029 A1 | 1/2017 | Raber et al. | |

(Continued)

FOREIGN PATENT DOCUMENTS

| | | | |
|---|---|---|---|
| WO | 2008/006226 A1 | 1/2008 | |
| WO | 2019/089583 A1 | 5/2019 | |
| WO | WO-2019089583 A1 * | 5/2019 | ........... A61K 31/015 |

OTHER PUBLICATIONS

European Search Report received for EP Patent Application No. 20814151.5, dated Jun. 12, 2023, 7 pages.

(Continued)

*Primary Examiner* — Svetlana M Ivanova

(74) *Attorney, Agent, or Firm* — Workman Nydegger

(57) ABSTRACT

Topical pain relief compositions include a cannabinoid, terpenoid, and skin penetration system that includes dimethyl sulfoxide (DMSO) and at least one compatibilizer. The composition may be in the form of an emulsion that contains water and at least one fatty component. The composition can be used to reduce or eliminate pain by direct topical application to an affected part or region of the body. A method of treating pain may include direct topical application of the composition to a joint, ligament, muscle, tendon, or disk. The composition penetrates through the skin to provide localized pain relief where applied and provides a quantity of cannabinoid in the region of the pain instead of distributing the cannabinoid systemically and/or to the brain or central nervous system. The composition may be applied by rubbing or massaging at the treatment site and/or by a bandage, patch or other barrier layer.

20 Claims, No Drawings

(56) References Cited

U.S. PATENT DOCUMENTS

| | | | |
|---|---|---|---|
| 2017/0266128 A1* | 9/2017 | Aung-Din | A61K 36/185 |
| 2018/0049994 A1 | 2/2018 | Aung-Din | |
| 2018/0064055 A1* | 3/2018 | Lewis | A01H 5/02 |
| 2019/0046438 A1 | 2/2019 | Hnat | |
| 2019/0142888 A1* | 5/2019 | Mojsa | A61K 31/352 |
| | | | 424/725 |
| 2019/0343760 A1 | 11/2019 | Aung-Din | |

OTHER PUBLICATIONS

International Preliminary Report on Patentability received for PCT Patent Application No. PCT/US2020/034984, dated Dec. 9, 2021, 7 pages.

International Search Report and Written Opinion received for PCT Patent Application No. PCT/US2020/034984, dated Aug. 19, 2020, 10 pages.

M. Verheijen, et al., "DMSO induces drastic changes in human cellular processes and epigenetic landscape in vitro", Scientific Reports, Mar. 15, 2019, https://www.nature.com/articles.

PainBomb CBD Brochure, retrieved Jun. 17, 2019.

* cited by examiner

PENETRATING TOPICAL PAIN RELIEF COMPOSITIONS AND METHODS OF USE

CROSS REFERENCE TO RELATED APPLICATION

This Application is a continuation of U.S. application Ser. No. 17/884,918, filed Aug. 10, 2022, which is a continuation-in-part of U.S. application Ser. No. 17/408,316, filed Aug. 20, 2021, now issued U.S. Pat. No. 11,446,278, which is a continuation-in-part of International Patent Application No. PCT/US20/34984, filed May 28, 2020, which claims the benefit of U.S. Prov App No. 63/015,652, filed Apr. 26, 2020, and U.S. Prov App No. 62/853,710, filed May 28, 2019, which are incorporated by reference in their entirety.

BACKGROUND OF THE INVENTION

1. Field of the Invention

The invention is in the field of topical/transdermal compositions that provide localized pain relief, including highly penetrating compositions that contain one or more cannabinoids and a skin penetration system.

2. Relevant Technology

Managing pain is a basic necessity of life. Pain can strike people of any age, gender and ethnicity without warning. Pain is a very strong motivator. People will do almost anything to relieve pain, especially constant pain that does not go away, including taking safe or dangerous medications, many of which are highly addictive and can cause problems worse than the underlying pain. The quest to relieve pain has contributed to the opioid crisis, which claims tens of thousands of lives annually.

Pain comes in many forms. Some results from injury; some results from disease. Many types of pain are close enough to the surface that they can be partially addressed by massage, liniments, and the like. Many people take daily doses of over-the-counter drugs such as non-steroidal anti-inflammatory drugs (NSAIDs) or acetaminophen for temporary relief thinking they are safe because of their ubiquitous use. However, long-term use of pain killers causes organ damage, connective tissue damage, ulcers, and tolerance. When these products stop working, many turn to stronger drugs, like opioids, which are highly addictive, quickly cause dependence, and often cause death.

Recently, focus has turned to legalized forms of *cannabis* and extracted cannabinoids to relieve pain. Delivery methods range from smoking weed, inhaling vaporized oils, and consuming edibles. Some forms are intoxicating while others are not. Systemic delivery can relieve pain but may affect other aspects of the body unrelated to the pain. Delivering an analgesic systemically when pain is localized requires orders of magnitude more analgesic than would otherwise be required if delivery were targeted.

While localized delivery of an analgesic is desirable, the skin acts as an almost impenetrable protective barrier that excludes most hydrophilic molecules such as water and hydrophobic molecules such as vegetable oils and cannabinoids. For this reason, topical *cannabis* products on the market today, such as lotions, gels, creams, roller bottles, and solid pushup stick products, provide little or no actual pain relief.

Many topical products contain one or more counterirritants such as menthol, methyl salicylate (oil of wintergreen), peppermint oil, and camphor, which provide the common cold-hot sensation of traditional liniments. While counterirritants provide the user with a sensation that is interpreted to mean the product is "working", they provide little or no therapeutic effect other than tricking the brain into focusing on the cold-hot sensation rather than the pain. Of the counterirritants, methyl salicylate may by metabolized to salicylic acid, a known NSAID. The fact that topical *cannabis* products typically contain one or more counterirritants implies that the cannabinoids themselves have little or no effectiveness in treating pain. The most likely reason is lack of adequate penetration through the skin where analgesia is needed.

Most topical CBD products list the amount of CBD in the container, which is often required by law. It is also effective marketing and can demand a price corresponding to the stated quantity of CBD. However, if the CBD is unable to penetrate through skin but remains on the skin surface, applying such products is just "painting" the skin. If the CBD cannot penetrate effectively through the skin, it cannot provide the advertised or desired pain-relief (other than perhaps relieving superficial skin irritation). The amount of CBD in the product is often a gimmick that bears no relationship to product effectiveness.

US 2016/0256411 to Aung-Din discloses a method of administering a cannabinoid to one specific region, i.e., to the back of the neck region at the hairline (BONATH), in order to deliver the cannabinoid directly to the brain stem and/or trigeminal nerves to provide pain relief to a different part or region of the body. This is called topical regional neuro-affective therapy ("TRNA therapy"). Aung-Din does not teach or suggest that such composition is effective in treating localized pain (e.g., arms, hands, legs, feet, ankles, knees, back, shoulder, or buttocks) by topical administration at the site of the pain for targeted local delivery and pain relief. By targeting interpretations of pain in the brain, Aung-Din is a form of indirect, non-targeted pain relief.

US 2011/0052694 to Stinchcomb et al. discloses a microneedle injection system designed to bypass the usual protective function of the epidermis to systemically deliver cannabinoid prodrugs. The microneedles form pores, holes or channels that provide a pathway for an otherwise non-penetrating composition to pass through the skin. Stinchcomb '694 reads like a pharmacopeia encyclopedia, listing literally thousands upon thousands of possible ingredients, including hundreds of unconnected range endpoints but no actual and meaningful ranges or amounts, and is devoid of examples of actual compositions or how to make them. None of the "Examples" disclose actual compositions. Nor does Stinchcomb '694 disclose that any composition was tested on a human to obtain useful and reliable feedback to determine if it would actually work to relieve pain.

US 2009/0247619 to Stinchcomb et al. similarly discloses cannabinoid-containing compositions that were tested on laboratory rats but not humans. Stinchcomb '619 provides no evidence that the product was effective to provide localized pain relief to a human. Rather, Stinchcomb '619 describes cutting and damage to tissue of laboratory test animals to determine whether the composition promoted tissue healing. Tissue wound healing, however, is not analogous to treating chronic pain or even acute pain, particularly nagging pain that has no obvious or diagnosable cause or treatment.

US 2013/0274321 to Newland discloses the treatment of skin cysts and other conditions using a composition comprising a dimethyl sulfoxide extract of *Cannabis sativa* flower and bud leaves that contain at least ten weight percent of tetrahydrocannabolinic acid (THCA). The flower and leaves were heated for five minutes at a temperature of 160-193° C., ground into a powder, mixed with dimethyl sulfoxide for 24 hours at room temperature, and filtered to yield the topical composition, which was applied topically or injected into a cyst. The amount of dimethyl sulfoxide in the topical composition used in Examples 2-14 was excessively high, at least 98 wt % based on the amounts of *cannabis* plant powder and dimethyl sulfoxide used in Example 1 to make the composition, which can be dangerous and highly irritating to the skin. In Examples 15-18, the composition was diluted to 70% DMSO with an unspecified diluent and injected into a cyst or fistula.

In view of the foregoing, there remains a need for improved compositions and methods that can provide localized topical delivery of cannabinoids to treat localized pain, maximize pain-relieving properties, and reduce or minimize unwanted side effects.

SUMMARY

It has now been found that cannabinoids can be effectively delivered topically to provide fast, effective, and localized pain relief using an appropriate skin penetration system. The topical pain relief compositions have been found to be highly effective in providing powerful localized analgesia to joints and muscles in various parts of the body, including arms, hands, fingers, legs, feet, ankles, knees, buttocks, back, shoulders, and neck.

In embodiments, a topical pain relief composition comprises a cannabinoid component and a skin penetration system comprising dimethyl sulfoxide (DMSO) and at least one compatibilizer. Example cannabinoids include but are not limited to cannabidiol (CBD) and/or tetrahydrocannabinol (THC). Example compatibilizers include alcohols, polyols, thiols, carboxylic acids, carboxylates, polycarboxylates, esters, amides, ethers, sulfonates, phosphonates, and amines. Water can be included to reduce skin irritation and possibly assist in penetration of the DMSO and cannabinoid(s) through the skin.

The compositions can advantageously include a terpenoid component that provides additional analgesia in addition to the cannabinoid component. Example terpenoids include α-pinene, β-pinene, camphene, β-myrcene, humulene, α-bisabolol, β-caryophyllene, linalool, camphor, limonene, ocimene, α-phellandrene, 1,8-ceneole, γ-terpinene, terpineol, fenchol, phytol, nerolidol, geranyl acetate, sabinene, p-cymene, β-phellandrene, valencene, borneol, isoborneol, geraniol, δ-3-carene, and terpinolene.

When properly formulated and proportioned, the various components interact together to maximize penetration and effectiveness of active pain-relieving components, while avoiding or minimizing irritation to the skin. DMSO is effective in penetrating through skin and carrying cannabinoids and terpenoids with it to provide powerful localized analgesia. However, it was found that there is a limit to how much of such compounds can effectively penetrate through the skin and provide effective pain relief when topically applied. In other words, there is an optimal range of cannabinoids and terpenes that will provide the most effective pain relief. When the optimal range is exceeded, efficacy is diminished. In other words, compositions containing greater amounts of combined cannabinoids and terpenoids can be less effective in relieving pain than compositions containing lesser amounts. This shows that effective penetration of cannabinoids and terpenoids through the skin is more important than their actual amounts in the formulation. It also means that pain relief compositions according to the invention may include less CBD than current compositions on the market, yet provide substantially greater pain relief.

Unexpectedly, the disclosed compositions have been found to be effective in treating, preventing, or reducing a wide variety of different types of pain, as shown in the Examples below. Test results suggest a synergistic interaction between the DMSO, compatibilizer, and cannabinoid(s), and possibly also the terpenoid(s), that is able to deliver a level of fast and lasting pain relief that was heretofore not possible using conventional topical analgesics.

In embodiments, the composition may comprise at least one fatty component, such as one or more fatty components selected from fatty acids, such as caproic acid, capric acid, caprylic acid, lauric acid, medium chain fatty acids (8 to 10 carbons), stearic acid, isostearic acid, octanoic acid, oleic acid, linoleic acid, or linolenic acid, esters of fatty acids, such as mono-, di- and/or triglycerides of fatty acids, preferably one or more of olive oil, sunflower seed oil, coconut oil, cocoa butter, jojoba oil, almond oil, pine needle oil, shea butter, argan oil, nigella *sativa* oil, beeswax, or flaxseed oil.

Although the fatty component would be expected to be inert and provide no pain relief, it was unexpectedly found that compositions that contain DMSO, one or more cannabinoids, one or more terpenoids, one or more fatty components, water, and at least one compatibilizer, which can be proportioned to form an emulsion, appear to work particularly well in providing pain relief, even better than solutions containing only DMSO and CBD and/or THC. Without being bound to any particular theory, it is postulated that the combination of DMSO, water, fatty component, and compatibilizer interacts with human skin to maximize penetration of the cannabinoid and optional terpenoid(s) through the skin. It is theorized that the combination causes localized softening of skin cells and/or opening of otherwise closed pores or pathways between or through the cells. It is further theorized that the fatty component forms a vapor barrier that forces the more hydrophilic components to penetrate through the skin.

In some embodiments, a bandage, barrier or patch can be used in combination with the composition to protect it from being wiped off or transferred before it has penetrated through the skin. A kit may include a container with the composition and one or more bandages or barriers for use in applying and/or placement over the composition.

In some methods of treatment, it may be advantageous to re-apply the composition one or more times after the previous application has penetrated through the skin to provide one more additional doses of pain relief. This can be particularly beneficial where the pain is located deeper below the skin and/or where the location of pain is difficult to access, e.g., where irritated tissue and/or nerves are blocked or impeded by bony and/or sinewy tissue.

The disclosed compositions have been found to be especially useful in treating chronic pain, including chronic muscle pain, chronic tendon pain, chronic ligament pain, and chronic idiopathic pain with no specific pathology or known cause, and in older (e.g., 50 or above) or infirm persons, who have tried traditional pain remedies but with little or no success.

It is to be understood that both the foregoing general description and the following detailed description are exemplary and explanatory only and are not restrictive of the embodiments claimed.

DETAILED DESCRIPTION OF THE PREFERRED EMBODIMENTS

Disclosed herein are topical pain relief compositions and methods for topical and/or transdermal delivery of one or more cannabinoids and optionally one or more terpenoids. A skin penetration system promotes effective penetration of the cannabinoid(s) and optional terpenoid(s) through dermal and underlying tissue where applied. The pain relief compositions are highly effective in providing powerful localized analgesia to joints, ligaments, muscles, tendons, nerves, and disks in various parts of the body, including arms, hands, fingers, legs, feet, ankles, knees, buttocks, back, shoulder, neck, and head.

In embodiments, a skin penetration system comprises dimethyl sulfoxide (DMSO) and at least one compatibilizer. Water and at least one fatty component have been found to further enhance effectiveness compared to DMSO alone. When properly formulated and proportioned, the various components synergistically interact together to maximize penetration and effectiveness of active pain-relieving components while avoiding or minimizing irritation to the skin. The skin penetration system has been found to be highly effective in penetrating through skin and underlying tissue and carrying cannabinoids and optional terpenoids with it to provide powerful localized analgesia.

DMSO is miscible with water and other hydrophilic substances and can dissolve several types of salts. However, DMSO is a relatively poor solvent for hydrophobic resins and waxes contained in crude *cannabis* oils, which contain useful cannabinoids and terpenoids. Even though CBD and THC isolates are soluble in DMSO, it has been found, surprisingly and unexpectedly, that solutions of DMSO and cannabinoid isolates on their own are quite ineffective in providing local pain relief when applied topically.

For this reason, compositions according to the invention advantageously include at least one compatibilizer, such as one or more amphiphilic organic compounds, which help compatibilize and stabilize compositions containing DMSO, at least one cannabinoid, at least one terpenoid, water, and at least one fatty component. It is hypothesized that compatibilized and stabilized compositions, including emulsions and suspensions where the components are substantially homogeneously mixed together, ensure close molecular proximity between individual DMSO, cannabinoid, and terpenoid molecules, while water, fatty component(s) and compatibilizer act to increase penetration and effectiveness of the pain relieving components of the composition.

In embodiments, the pain relief compositions comprise 8-80%, 11-75%, or 15-70% DMSO by weight, such as greater than 11%, 15%, 20%, 25%, 30%, 35%, 40%, 45%, 50%, or 60% DMSO by weight and less than 80%, 75%, or 70% DMSO by weight.

Example compatibilizers are amphophilic organic compound that include a hydrocarbon lipophilic portion and a polar hydrophilic portion with one or more heteroatoms (O, N, S). Examples include alcohols, polyols, thiols, carboxylic acids, carboxylates, polycarboxylates, esters, amides, ketones, aldehydes, ethers, sulfonates, phosphonates, and amines.

Examples of compatibilizers that are more hydrophilic and less hydrophobic include, but are not limited to, glycerin, amino acids, propylene glycol, 1,3-propanediol, 1,3-butanediol, sorbitol, xylitol, glucosides, sorbitan, polyethylene glycol, polysorbate, alcohols, lower fatty acids, triethanolamine, carboxylic acids, polycarboxylic acids (e.g., partially neutralized polyacrylic acids), lower esters, ethyl acetate, acetoacetic ester, 2-(2-ethoxyethoxy)ethanol, hydroxyacid esters, and ketones.

Examples of compatibilizers that are less hydrophilic and more hydrophobic include glycerides, isostearic acid, octanoic acid, oleic acid, oleyl alcohol, lauryl alcohol, ethyl oleate, isopropyl myristate, butyl stearate, methyl laurate, diisopropyl adipate, glyceryl monolaurate, tetrahydrofurfuryl alcohol, polyethylene glycol ether, polyethylene glycol, diethylene glycol monomethyl ether, diethylene glycol monoethyl ether, alkylaryl ethers of polyethylene oxide, polyethylene oxide monomethyl ethers, polyethylene oxide dimethyl ethers, and N-alkylpyrrolidone. Such materials may constitute a fatty component depending on hydrophobicity.

It was discovered that DMSO, when used with a compatibilizer to form a skin penetration system, is effective in carrying cannabinoids and terpenoids through the skin to provide localized pain relief. Cannabinoids and terpenoids have been found to be largely insoluble and form cloudy mixtures in solutions containing 70% DMSO and water, particularly waxy forms of extracted cannabinoids. DMSO is often used by itself in a 70% aqueous solution or gel to reduce or minimize skin irritation compared to more concentrated forms of DMSO. Adding a compatibilizer to replace or augment at least some of the water used to dilute DMSO in topical formulations substantially improves the effectiveness of the topical pain relief compositions compared to using only water. The compatibilizer can also provide skin soothing properties and act as an emollient.

It was further discovered that, while a skin penetration system containing DSMO and at least one compatibilizer is highly effective in facilitating penetration of hydrophobic cannabinoids and terpenes through the skin to provide localized pain relief, there is a limit to how much of such hydrophobic compounds can effectively penetrate through the skin when a dollop of pain relief composition is applied topically to skin. By adding different amounts of cannabinoids and terpenes to the skin penetration system and testing the different topical pain relief compositions, it was discovered that there is an optimal range of cannabinoids and terpenes that will provide the most effective pain relief. When the optimal range was exceeded, the topical pain relief composition appeared to be no more effective than compositions containing lower amounts of cannabinoids and terpenoids. In some cases, compositions that included greater amounts of cannabinoids and terpenoids were less effective in relieving pain than compositions containing lower amounts. This demonstrates that effective penetration of the cannabinoids and terpenoids through the skin is far more important than their actual amounts in the formulation. It also means that topical pain relief compositions according to the invention may include less CBD and/or THC than current compositions on the market yet provide substantially greater pain relief. This is demonstrated in the Examples below.

Example cannabinoids that can be useful in providing analgesia and other benefits include but are not limited to tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), tetrahydrocannabivarin (THCV), cannabicyclol (CBL), cannabidivarin (CBDV), cannabichromevarin (CBCV), and cannabigerovarin (CBGV). CBD is legal nationwide, highly effective, and a preferred cannabinoid. THC has several isomers. The main psychoactive component of *cannabis* is delta-9-tetrahydrocannabinol. Another type is delta-8-tetrahydrocannabinol. Yet another is delta-11-tetrahydrocannabinol.

In some embodiments, the composition includes two or more cannabinoids, such as CBD and THC, particularly CBD and delta-8-tetrahydrocannabinol but also CBD and delta-9-tetrahydrocannabinol or CBD and delta-11-tetrahydrocannabinol. Evidence has shown that combining CBD and THC provides faster and/or greater pain reduction than either CBD or THC alone.

In embodiments, the amount of the one or more cannabinoids can be in a range from about 0.003% to about 5%, about 0.004% to about 4%, about 0.005% to about 3%, about 0.008% to about 2%, about 0.01% to about 1.5%, about 0.02% to about 1%, about 0.03% to about 0.7%, about 0.04% to about 0.5%, about 0.05% to about 0.4%, about 0.06% to about 0.3%, or about 0.07% to about 0.2%, by weight of the composition, or any range using any two of the foregoing lower and upper endpoints. In other embodiments, such as more highly penetrating liquid compositions, the one or more cannabinoids can be in a range from about 0.05-10%, or 0.08-8%, or 0.1-6%, or 0.13-5%, or 0.15-4%, or 0.2-3%, or 0.3-2%, by weight of the composition, or any range using any two of the foregoing lower and upper endpoints.

In embodiments, the cannabinoid component can be water soluble or water dispersible, such as liposomal droplets, aqueous nanosized cannabinoid dispersion, water-in-oil emulsion, or oil-in-water emulsion.

To provide an additional analgesic effect beyond that provided by the one or more cannabinoids, the topical pain relief compositions advantageously include one or more terpenoids. Example terpenoids include α-pinene, β-pinene, camphene, β-myrcene, humulene, α-bisabolol, β-caryophyllene, linalool, camphor, limonene, ocimene, α-phellandrene, 1,8-ceneole, eucalyptol, γ-terpinene, terpineol, fenchol, phytol, nerolidol, geranyl acetate, sabinene, p-cymene, β-phellandrene, valencene, borneol, isoborneol, geraniol, δ-3-carene, and terpinolene. The topical pain relief compositions include at least one, typically at least two, preferably at least three, more preferably at least four, and even more preferably at least five, of the foregoing terpenes.

In some embodiments, topical pain relief compositions may include, in approximate or suggested order of prevalence: linalool, α-pinene, β-myrcene, β-caryophyllene, and humulene.

In other embodiments, topical pain relief compositions may include, in approximate or suggested order of prevalence: β-myrcene, limonene, β-caryophyllene, humulene, linalool, β-pinene, α-pinene, α-bisabolol, terpineol, fenchol, phytol, nerolidol, geranyl acetate, camphene, and optionally a proprietary blend of 7 additional terpenes.

In yet other embodiments, topical pain relief compositions may include, in approximate or suggested order of prevalence: linalool, β-myrcene, limonene, β-caryophyllene, α-pinene, humulene, β-pinene, α-bisabolol, terpineol, fenchol, phytol, nerolidol, geranyl acetate, camphene, and optionally a proprietary blend of 7 additional terpenes.

The relative amounts and quantity of total terpenoids can be selected to provide a desired pain relief profile. The amount of each terpenoid can be expressed as a percentage of total terpenoids. The combined amount of terpenoids can be expressed as a ratio of total terpenoids to total cannabinoids. In some embodiments, the ratio (w/w) of total terpenoids to total cannabinoids can be in a range of about 1:20 to about 10:1, about 1:15 to about 7:1, about 1:10 to about 5:1, about 1:9 to about 3:1, about 1:7 to about 2:1, about 1:6 to about 1.5:1, about 1:5 to about 1.2:1, or about 1:4 to about 1:1, by weight, or any range using any two of the foregoing lower and upper endpoints.

The amount of the one or more terpenoids can be in a range from about 0.002% to about 4%, about 0.003% to about 3%, about 0.005% to about 2.5%, about 0.008% to about 2%, about 0.01% to about 1.5%, about 0.02% to about 1%, about 0.03% to about 0.7%, about 0.04% to about 0.5%, about 0.05% to about 0.4%, about 0.06% to about 0.3%, or about 0.07% to about 0.2%, by weight of the composition, or any range using any two of the foregoing lower and upper endpoints. In other embodiments, The composition may include other components, such as essential oils, which typically include a blend of terpenoids, aspirin (acetyl salicylic acid), other NSAIDs or analgesics, methyl salicylate, menthol, *arnica* oil, spikenard, peppermint oil, oil of wintergreen, or mixed pine terpenes, such as pure gum spirits of turpentine, which primarily contains α-pinene and β-pinene, with lesser amounts of carene, camphene, dipentene, and terpinolene.

To provide effective penetration of the active pain-relieving components, the topical pain relief pain compositions advantageously contain greater than 35%, 40%, 45%, 50%, 55%, or 60% by combined weight of DMSO and compatibilizer(s). In other embodiments, the compositions advantageously contain greater than 35%, 40%, 45%, 50%, 55%, or 60% by combined weight of DMSO, compatibilizer(s), and water. In embodiments, the skin penetration system comprises DMSO and a compatibilizer in which the ratio of DSMO to compatibilizer is greater than 1:1 by weight, such as a ratio of DMSO to compatibilizer(s) ranging from about 1:3 to about 30:1, or about 1:2 to about 20:1, or about 1:1.5 to about 15:1, or about 1:1 to about 12:1, or about 1.5:1 to about 10:1, or about 2:1 to about 8:1, or about 2.5:1 to about 7:1, or about 3:1 to about 6:1, by weight.

In embodiments, the composition can be an emulsion or suspension in which the more hydrophilic compounds, including DMSO, hydrophilic compatibilizer(s), and water, form a continuous phase and the more hydrophobic compounds, including cannabinoids, terpenoids, and hydrophobic compounds, are dispersed as a discontinuous phase. It is especially beneficial for cannabinoids and terpenoids to be dispersed as tiny droplets, preferably nano-sized droplets between about 5-1,000 nm, such as about 10-600 nm, or about 15-400 nm, or about 20-200 nm, in size.

To maintain a stable emulsion or suspension in which the cannabinoids and terpenoids remain as tiny highly dispersed droplets, the composition may include a gel-forming agent, examples of which include carbomer, polyethylene oxides, poloxamers, vegetable gums, gelatin, pectin, alginates, agar, polysaccharides, proteins, and the like. It is beneficial to limit the amount of such components to no more than about 5%, 4%, 3%, 2%, 1%, 0.5%, or 0.25% by weight of the composition. The gel-forming agent is typically amphiphilic and may augment the compatibilization effects of other compatibilizers. However, because of their generally large molecular structures, gel-forming agents will typically not penetrate beyond the outer epidermal layer.

In some embodiments, the composition can include at least one fatty component, such as one or more fatty components selected from fatty acids, such as caproic acid, capric acid, caprylic acid, lauric acid, medium chain fatty acids (6-12 or 8-10 carbons), stearic acid, isostearic acid, octanoic acid, oleic acid, linoleic acid, or linolenic acid, esters of fatty acids, such as mono-, di- and/or triglycerides of fatty acids, preferably one or more of olive oil, sunflower seed oil, coconut oil, cocoa butter, jojoba oil, almond oil, pine needle oil, shea butter, argan oil, nigella *sativa* oil, beeswax, and flaxseed oil, and α-tocopheryl acetate. Amphiphilic fatty components, such as lower fatty acids and esters, may function as a compatibilizer.

Although the fatty component would be expected to be inert and provide no pain relief, it was unexpectedly found that compositions that contain DMSO, one or more cannabinoids, one or more terpenoids, one or more fatty components, water, and at least one compatibilizer, which can be proportioned to form an emulsion, appear to work particularly well in providing pain relief, even better than solutions containing only DMSO and CBD and/or THC. Without being bound to any particular theory, it is postulated that the combination of DMSO, water, fatty component, and compatibilizer interacts with human skin to maximize penetration of the cannabinoid and optional terpenoid(s) through the skin. It is theorized that the combination causes localized softening of skin cells and/or opening of otherwise closed pores or pathways between or through the cells. It is further theorized that the fatty component forms a vapor barrier that forces the more hydrophilic components to penetrate through the skin.

In some embodiments, a bandage, barrier or patch can be used in combination with the topical pain relief composition to protect it from being wiped off or transferred before it has penetrated through the skin. A kit may include a container with the composition and one or more bandages or barriers for use in applying and/or placement over the composition. A kit of one or more patches loaded with the composition may be provided.

In some methods of treatment, it may be advantageous to re-apply the composition one or more times after the previous application has penetrated through the skin to provide one more additional doses of pain relief. This can be particularly beneficial where the pain is located deeper below the skin and/or where the location of pain is difficult to access, e.g., where irritated tissue and/or nerves are blocked or impeded by bony and/or sinewy tissue.

The composition can have a form selected from cream, lotion, gel, suspension, ointment, high-viscosity liquid, medium viscosity liquid, or low viscosity liquid. The composition is advantageously in the form of a cream, gel, or liquid to enhance the ability to penetrate through the skin to provide local pain relief. In general, the ability of the compositions to quickly and effectively penetrate through the skin greatly enhances efficacy and reduces the amount of cannabinoids and terpenoids required to provide pain relief, both therapeutic and prophylactic.

The amount of CBD or other cannabinoid required to provide local pain relief can be about 5 mg or less, 3 mg or less, 2 mg or less, 1.5 mg or less, 1 mg or less, 0.75 mg or less, or 0.5 mg or less. By comparison, the amount of CBD or other cannabinoid, when orally administered, that is required to provide a therapeutic effect is reportedly 10 mg or more, 15 mg or more, 20 mg or more, or 25 mg or more. Topical compositions that cannot penetrate through the epidermis may provide the same or more cannabinoids and yet provide little or no pain relief. Therefore, the important thing is the bioavailable dose, not dosage per se.

Similarly, the amount of total terpenoids required to provide local pain relief can be about 5 mg or less, 3 mg or less, 2 mg or less, 1.5 mg or less, 1 mg or less, 0.75 mg or less, 0.5 mg or less, 0.3 mg or less, or 0.1 mg or less.

The pain relief compositions are advantageously not provided as a thick waxy composition as is common with many commercially available topical CBD formulations, which appear to remain as a coating on the skin where applied.

The composition can be provided as a muscle rub, massage oil, spray, or roll-on.

Pain relief compositions disclosed herein have been found to be effective in providing rapid and lasting relief for a wide range of muscular, joint and other pain conditions including, but not limited to, neck pain, shoulder pain, muscular pain, back pain, joint pain, knee pain, hamstring pain, arm pain, tennis elbow, bunions, ankle pain, foot pain, hand pain, finger joint pain, wrist pain, pinched nerves, degenerated disc, headaches, plantar fasciitis, and pain resulting from neuromuscular conditions, such as multiple sclerosis, Parkinson's disease, and cancer. The compositions have also been found to be effective to provide prophylactic relief, such as pre-workout or prior to intense activity to prevent or reduce subsequent pain from happening that would normally occur. Examples include prior to lifting weights, hiking, biking, running, tennis, golf, playing drums, guitar or other musical instrument, typing at a computer, and driving a car.

EXAMPLES

The following Examples include descriptions of comparative CBD- and THC-containing compositions (i.e., commercial formulations) which were found to provide little or no pain relief and penetrating topical pain relief compositions of the disclosed invention, which were found to be substantially more effective in providing pain relief than the comparative compositions, typically at the same or lesser percentage and/or dosage of cannabinoid.

Comparative Example A

A CBD balm was provided in the form of a waxy pushup stick similar to a common deodorant stick, with a solid composition that is advanced using a twist knob within an oval plastic container and mating shell top. The label states the CBD balm is "extra strength advanced heated relief" containing 200 mg CBD in 2.5 oz (75 g) of total balm (0.267% CBD w/w). The ingredients (not in order of prevalence) are: "Cannabidiol (CBD), Menthol Crystals (DL-Menthol), Camphor Oil (*Cinnamomum Camphora*), Arnica Montana Extract (*Helianthus Annus*), Peppermint Oil (*Mentha Piperita*), Beeswax (Cera Alba), Coconut Oil (*Cocos Nucifera*), Grapeseed Oil (*Vitis* Vinfera), Eucalyptus Oil (*Eucalyptus Globulus* Leaf Oil), Vitamin E (Tocopherol), Caffeine Oil, Proprietary Scent."

A 58-year-old man suffering from constant neck and shoulder pain for several weeks purchased Comparative Example A from an alternative medicine clinic with the goal of obtaining pain relief. The subject applied the product to the affected area and immediately felt a cooling sensation and noticed the smell of menthol and other aromatics in the balm. However, the man experienced no pain relief even though the cooling sensation and smell persisted for hours.

A male body builder in his late 30s suffering from inner tendonitis at the elbow where the bicep muscle attaches to the ulna applied the CBD balm and experienced no pain relief.

A 54-year-old man who is an ultra-marathon runner and avid hiker had been suffering from sharp bunion pains in both feet. The subject applied the CBD balm to sore areas in the foot and experienced no pain relief.

A 30-year-old professional skier applied the CBD balm to sore muscles and joints and experienced no pain relief.

It is hypothesized that the CBD was unable to provide pain relief because it could not penetrate through the skin but remains on the surface with other oily components. In comparison, pain relief compositions of the disclosed invention (e.g., Examples 1-10) containing less than half the concentration of CBD (about 66.7 mg CBD in 2 oz (60 g) of composition, or 0.11% CBD) were highly effective in providing pain relief within minutes or seconds of application. In one case, a pain relief composition similar to Example 2 below was applied to the affected area over the top of the previously applied CBD balm of Comparative Example A and provided significant pain relief. This demonstrated that penetration of the inventive composition through the skin was not impeded by the previously applied CBD balm and was the critical factor affecting relief.

Comparative Example B

A CBD balm was provided in the form of a lotion in a pump bottle that reportedly contains 250 mg "full CBD" in 1 ounce (0.845% w/v) and provides "8 mg per pump". The label instructs the user to "apply directly to skin, muscles & joints". The listed ingredients are "250 mg of cannabidiol (CBD) from *Cannabis sativa* L (whole hemp plant" . . . , All-Natural Aloe Leaf Juice, Meadow-Foam Seed Oil, Camphor Bark Oil Menthol Crystals, *Capsicum* Fruit Ole-Resin, Roman and German Chamomile Flower, Cinnamon Leaf Oil, Citronella Oil, *Eucalyptus* Leaf Oil, Helichrysum Flower Oil, Ginger Root Ooil, Pink Grapefruit Peel Oil, Juniper Berry Oil, Lemon-Grass Oil, Peppermint Oil, Pine Needle Oil, Ravensara Oil, Rosemary Leaf Oil, Spearmint Oil, Wild Oregano Oil, Glycerin, Tetrasodium Glutamate Di-acetate, Alcohol, Phenoxyethanol, Carbomer Triethanolamine, Which Hazel Water."

The 58-year-old man who suffered from neck and shoulder pain purchased Comparative Example B from a local pharmacy, which said it won awards for best topical CBD, applied it to a sore joint, felt a cooling sensation, and noticed the smell of menthol, mint and other aromatics in the balm. However, the subject experienced little to no pain relief although the product purportedly contained about three times the concentration of CBD compared to the composition of Comparative Example A.

The 54-year-old ultramarathon runner applied the CBD balm to sore areas in the foot and experienced no pain relief.

It is hypothesized that there is minimal penetration of the CBD component through the skin. In comparison, pain relief compositions of the disclosed invention (e.g., Examples 1-10) containing about one-seventh the quantity of CBD (about 66.7 mg CBD in 2 oz (60 g) of composition) (0.11% CBD) were highly effective in providing pain relief within minutes or seconds of application.

Comparative Example C

Synergy Relief CBD & THC Infused Balm sold by Planet 13, Las Vegas, Nevada, reportedly contains 50 mg CBD and 50 mg THC in 1.7 oz (50 g) of the balm (0.1% CBD w/w and 0.1% THC w/w).

The label for the Synergy Relief product used in this example listed the following ingredients (presumably in order of prevalence): olive oil (extra virgin), *lobelia* olive oil, beeswax, castor oil, CBD isolate, cocoa butter, essential oil blend (proprietary), and THC. The total cannabinoid analysis in 100 mg of cannabinoids: 45.939 mg THC, 49.824 mg CBD, 0.0 mg CBG, 4.191 mg THCV, and 0.0 mg THCVa. Total terpenes in the product were: eucalyptol 13.546 mg, camphene 9.220 mg, alpha-pinene 24.648 mg, and linalool 11.024 mg.) The weight ratio of total terpenoids (58.438 mg) to total cannabinoids (99.954 mg) was therefore 0.585:1, or a little more than 1:2.

A more recent label for a different lot of Synergy Relief CBD & THC Infused Balm listed the following ingredients (presumably in order of prevalence): Infused Olive Fruit Oil (*Olea Europaea* Fruit Oil), Isopropyl Alcohol, *Lobelia Inflata* Seed Extract, Cara Alba (Beeswax), *Ricinus Communis* (Castor) Seed Oil, Theabroma Cacao (Cocoa) Seed Butter, Rosemarinus *Officinalis* (Rosemary) Oil, THC Oil, CBD Oil, Lavadula *Officinalis* (Lavender) Flower Oil, *Cedrus Deodara* (Cedarwood) Oil, *Pinus Sylvestris* (Pine) Needle Oil."

The 58-year-old man suffering from neck and shoulder pain applied the CBD & THC Infused Balm several times to the affected area but experienced no noticeable pain relief. The composition of Comparative Example C was modified as disclosed herein by mixing it with a skin penetration system that included DMSO. The 58-year-old man applied the modified composition to the neck and shoulder and, rather surprisingly and unexpectedly, obtained fast, effective, and long-lasting pain relief.

The 54-year-old ultramarathon runner applied the CBD & THC Infused Balm to sore areas in the foot and experienced no pain relief. The 54-year-old man applied the modified composition (according to the invention) to the same sore areas of the foot and obtained fast, effective, and long-lasting pain relief.

Comparative Example D

A commercially available THC-infused muscle relief lotion comprises 112.5 mg CBD in 4 oz (118 mL) of the lotion (0.1% THC w/v). The label listed the following ingredients (presumably in order of prevalence): infused olive fruit oil (*Olea* Europa Fruit Oil), isopropyl alcohol, *lobelia inflata* seed extract, aloe barbadensis leaf juice, water, *Cocos nucifera* (coconut) fruit oil, emulsifying wax, mixed natural tocopherols, *Theobroma cacao* (cocoa) seed butter, *Rosmarinus officinalis* (rosemary) oil, *Lavandula officinalis* (lavender) flower oil, *cedrus deodara* (cedarwood) oil, *Pinus sylvestris* (pine) needle oil, boswellia *serrata* (frankincense) gum oil, and cannbis oil. The terpene analysis for the product was: alpha-pinene 3.432 mg/g, linalool 2.013 mg/g, and limonene 1.832 mg/g.

A 59-year-old man suffering from various muscle and joint pains applied Comparative Example D to affected areas but experienced little or no pain relief.

Comparative Example E

A DMSO cream with aloe vera (rose scented) contained 70% DMSO, 30% aloe vera in a cream base was purchased online. The 58-year-old man suffering from constant neck and shoulder pain for several weeks first applied the DMSO cream to the affected area and possibly obtained some pain relief, but only briefly. However, the rose smell was strong and made the man feel nauseous and self-conscious. The pain returned as usual.

Comparative Example F

A solution containing primarily DMSO and CBD was made and applied by the 58-year-old man to various places where the inventive composition was found to provide effective pain relief. It was believed that removing fatty components and other inert materials that are not known to provide pain relief would make the composition more effective. In fact, the composition was largely ineffective, providing little to no noticeable pain relief. This was surprising and unexpected and appears to point to the importance of including the compatibilizer, water, and one or more fatty components, in addition to the DMSO, cannabinoid(s), and optional terpenes.

Comparative Example G

A solution containing primarily DMSO and a blend of terpenes containing, among other things, linalool, α-pinene, 8-myrcene, 8-caryophyllene, and humulene, was made and applied by the 58-year-old man to various places where the inventive composition was found to provide effective pain relief. There are reports of terpenes contributing some or most of the pain relief offered by *cannabis* extracts. The composition was ineffective, providing no noticeable pain relief. While terpenes can help provide an entourage effect when combined with one or more cannabinoids, they were ineffective by themselves when applied using DMSO as the carrier.

Example 1

The Synergy Relief CBD & THC Infused Balm of Comparative Example C was mixed with pharmaceutical grade (99.995%) DMSO at a ratio of about 1:1. The resulting topical composition was a thin runny suspension that separated into phases and required agitation before use. Addition of about 10% of vegetable glycerin helped to stabilize the composition somewhat. The composition contained about 0.05% w/v CBD and about 0.05% w/v THC, or about 0.1% total cannabinoids and about 0.06% total terpenes.

The 58-year-old man suffering from constant neck and shoulder pain for several weeks, who had previously tried Comparative Examples A, C and E, applied Example 1 to the neck and shoulder area and experienced nearly total pain relief within about 5 minutes. The pain relief lasted for about 12 hours. The subject re-applied the composition 2-3 times per day for 3-4 days, has obtained essentially permanent pain relief, and has been able to manage and eliminate the pain if it arises. Whatever pain does arise from time to time is substantially less than the pain prior to first using Example 1 but after multiple applications of Comparative Examples A, C and E to the affected area.

The 54-year-old ultra-marathon runner applied the composition of Example 1 to both feet and noticed a pain reduction of about 50-70% in 10-20 minutes. The man re-applied the composition before going to bed. The next morning the man awoke with virtually no pain in either foot.

Example 2

A commercially available CBD hand and body lotion (CBD SFV/Klashnikova Terpenes—Migraine & Pain) sold by Koodegras (Sandy, Utah), which reportedly contains 400 mg CBD in 6 fluid ounces of lotion (0.225% w/v) in a glass jar, was mixed with DMSO and glycerin to form a topical composition in the following amounts:

| CBD Lotion | 40 grams |
|---|---|
| DMSO (99.995%) | 30 milliliters |
| Glycerin | 10 milliliters |

The label for the CBD hand and body lotion listed the following ingredients (presumably in order of prevalence): "Purified water, Capric/Caprylic Triglycerides, (Sunflower) Seed Oil, Hemp CBD Oil with Terpenes, Moroccan Organic Argan Oil, Emulsifying Wax, Glyceryl Monostearate, *Simmondsia* (jojoba) oil, Butyrospermum Parkii (Shea Butter), Stearic Acid, Cetyl Alcohol, Glyceryl Distearate, and Carbomer." The CBD hand and body lotion inherently contained the following terpenes/terpenoids (in approximate order of prevalence): linalool, myrcene, limonene, β-caryophyllene, α-pinene, humulene, β-pinene, α-bisabolol, terpineol, fenchol, phytol, nerolidol, geranic acid, camphene, and a proprietary blend of 7 additional terpenes. The ratio of CBD to terpenes was about 3 parts CBD to about 1-2 parts total terpenoids by weight.

The resulting topical composition of Example 2 contained about 0.11% CBD w/v, with a ratio of about 3 parts CBD to about 1-2 parts total terpenoids by weight, and was a thin cream that remained as a stable emulsion.

The 58-year-old man suffering from constant neck and shoulder pain for about one month, who had previously applied Example 1 to the neck and shoulder, applied Example 2 to the neck and shoulder area after some of the pain returned and experienced nearly total pain relief in 10-20 minutes. The pain relief lasted about 12 hours. The composition was re-applied for the next few days with similar results. This product was used for several weeks and provided the subject with virtually total and lasting pain relief.

The 54-year-old ultra-marathon runner applied the composition of Example 2 to both feet and obtained fast, effective and long-lasting pain relief. The man has been using this composition to scale numerous mountains and run ultramarathons ever since and attributes his ability to effectively manage the pain associated with these hard physical activities to Example 2 and similar compositions.

The male body builder who applied Comparative Example A applied the composition of Example 2 to the affected area and obtained relief, even after applying this composition over the top of previously applied Comparative Example A. The man had been scheduled for surgery to repair the arm tendon, but after 4 months of using Example 2 and similar compositions of the invention, and performing physical therapy, he and his surgeon cancelled the surgery.

Example 3

A commercially available CBD black seed salve (Sacred Herbal Medicinal Remedies) sold by Koodegras, which reportedly contains 900 mg CBD in 6 fluid ounces (0.5% CBD w/v), was mixed with DMSO (99.995%) and glycerin to form a topical composition in the following amounts:

| CBD Salve | 40 grams |
|---|---|
| DMSO | 30 milliliters |
| Glycerin | 10 milliliters |

The label for the CBD black seed salve listed the following ingredients (presumably in order of prevalence): Organic Olive Oil, Black Seed (Cumin) Oil, Coconut Oil, Jojoba Oil, Sweet Almond Oil, Argan Oil, Nigella *Sativa* Oil, Shea Butter, Beeswax, Hemp CBD Oil, Skullcap Charcoal, *Arnica*, Passionflower, Vitamin E, Tocopherol, Camphor, White Willow Oil, Rosemary, Turmeric Lavender, Frankincense, *Capsicum* Annum, And Essential Oils And Herbal Blends (Proprietary).

The resulting topical composition contained about 0.25% CBD w/v, with a ratio of about 3 parts CBD to about 1-2 parts total terpenoids by weight and was a thick emulsion that appeared to be relatively stable overnight.

The 58-year-old man suffering from nagging pain in the left shoulder and neck area for about one month applied the topical composition to the area when some of the pain returned and experienced substantial pain relief. The composition left a heavier oily skin residue compared to the composition of Example 2 and did not appear to penetrate as completely.

A 48-year-old man suffering from arm pain that impaired his golf swing applied the composition and obtained almost total relief. The only side effect was a funny taste in his mouth, which was likely from the black seed *sativa* components. He shared the composition with a golfer friend who had intense shoulder pain, which had prevented his natural swing, and he was able to resume golfing with his normal swing.

Example 4

The composition of Example 3 was mixed with an additional 40 milliliters of DMSO (99.995%) and 5 milliliters of glycerin to form a thinner, runny material, which separated into layers over time (about 0.167% CBD w/v). The composition was agitated before application, was more penetrating, left less residue than the composition of Example 3, and provided about the same pain relief as Examples 1 and 2.

Example 5

A commercially available CBD salve (No. 9 Time-Released Quick Relief Salve) sold by Koodegras, which reportedly contains 200 mg CBD in 2 fluid ounces (0.338% CBD), was mixed with DMSO (99.995%) at a ratio of 1:1 to form a topical composition.

The label for the CBD No. 9 salve listed the following ingredients (presumably in order of prevalence): Argan Oil, Black Seed Oil, Olive Oil, Organic Beeswax, Proprietary Asian Herbal Mix, Vitamin E Oil, Mixed Tocopherols, Anhydrous Hemp Oil, Time Release CBD Oil, Proprietary Essential Oil Blend, *Melaleuca* Oil, *Eucalyptus* Oil, Cayenne Oil, And Beta-Caryophyllene.

The resulting topical composition contained about 0.169% CBD w/v with a ratio of about 3 parts CBD to about 1-2 parts total terpenoids by weight and was a thick emulsion that was relatively stable and required occasional agitation to resuspend. Addition of vegetable glycerin helped stabilize the composition, reduce odor of the DMSO, and yielded a composition containing about 0.15% CBD w/v and associated terpenoids.

A person suffering from pain applied the topical composition to the area where pain was experienced and obtained nearly total pain relief that lasted about 12-24 hours. The composition was re-applied as needed and provided consistent pain relief.

Example 6

A commercially available water-borne nanosized CBD dispersion (Angstrom Plexll phytocannabinoid complex) sold by Koodegras, which reportedly contains 250 mg CBD in 10 milliliters (2.5% CBD w/v), was mixed with DMSO (99.995%) at a ratio of 1:1 to form a topical composition containing about 1.25% CBD.

The label for the CBD Angstrom Plexll dispersion listed the following ingredients (presumably in order of prevalence): Purified Water, Olive Oil, Sunflower Lecithin, Anhydrous Hemp Oil, Potassium Sorbate, Vitamin E, And Citric Acid.

The resulting topical composition was a thin non-viscous fluid suspension that was relatively stable but may require occasional agitation to resuspend. Addition of vegetable glycerin appears to have stabilized the suspension and reduced the odor of the DMSO.

A person suffering from pain applied the topical composition to the area where pain was experienced and obtained nearly total pain relief that lasted about 12-24 hours. The composition was re-applied as needed and provided consistent pain relief.

Examples 7A-7R

Examples 7A-7R were made by mixing Base Composition A as a source of CBD and terpenoids with other components to yield topical pain relief compositions. Base Composition A was an emulsion manufactured for the inventor in 1-gallon amounts and contained a quantity of hemp CBD oil that provided 10,000 mg of CBD per gallon (0.264% CBD w/v) and terpenoids in a ratio of about 3 parts CBD to about 1-2 parts total terpenoids by weight.

Base Composition A

Base Composition A contained the following in order of prevalence:

Purified water

Capric/Caprylic Triglycerides

Sunflower Seed Oil

Hemp CBD Oil with Terpenes

Moroccan Organic Argan Oil

Emulsifying Wax

Glyceryl Monostearate

*Simmondsia* (jojoba) oil

Butyrospermum Parkii (Shea Butter)

Stearic Acid

Cetyl Alcohol

Glyceryl Distearate

Carbomer.

The ratio of CBD to total terpenes was about 3 parts CBD to about 1-2 parts total terpenoids. The relative amount of each terpenoid as a percentage of total terpenoids was approximately:

| | |
|---|---|
| Linalool | 75% |
| α-Pinene | 11% |
| β-Myrcene | 10.5% |
| β-Caryophyllene | 2% |
| Humulene | 1.5% |

Base Composition A ("A") was mixed with components in the amounts in Tables 1 and 2 to yield the compositions of Examples 7A-7P.

TABLE A

| Component | 7A | 7B | 7C | 7D | 7E | 7F | 7G | 7H | 7I |
|---|---|---|---|---|---|---|---|---|---|
| A | 25 g | 40 g | 250 g | 80 g | 160 g | 300 g | 200 g | 300 g | 500 g |
| DMSO | 20 ml | 40 ml | 250 ml | 80 ml | 160 ml | 300 ml | 200 ml | 300 ml | 500 ml |
| Glycerin | 1 g | 10 ml | 62.5 ml | 20 ml | 40 ml | 75 ml | 50 ml | 75 ml | 125 ml |
| Gel (70/30 DMSO:Water) | 2 g | 10 g | 60 g | 20 g | 40 g | 70 g | 70 g | 70 g | 100 g |
| *White Camphor | 0.5 ml | 0.5 ml | 2 ml | 1.25 ml | 1.5 ml | 1.5 ml | 2 ml | 3 ml | 6 ml |
| Oil of Wintergreen | | | | | | 2 ml | 2 ml | 3 ml | 6 ml |
| Arnica | | | | | | 3 ml | 2 ml | 2 ml | 4 ml |
| Mixed pinenes | | | | | | | | | 6 ml |

*White Camphor: α-Thujene (0.33%), α-Pinene(2.3%), camphene (0.99%), sabinene + β-pinene (13%), 6-methyl-5-heptene-2-one (0.11%), β-Myrcene (9.24%), δ-2-carene (0.1%), α-phellandrene (3.63%), δ-3-carene (0.23%), α-terpinene (5.01%), p-cymene (9%), 1,8-cineole + β-phellandrene + limonene (55.17%), γ-terpinene (0.06%), and α-terpinolene (0.03%)

TABLE B

| Component | 7J | 7K | 7L | 7M | 7N | 7O | 7P | 7Q | 7R |
|---|---|---|---|---|---|---|---|---|---|
| A | 600 g | 800 g | 160 | 70 g | 600 g | 600 g | 600 g | 200 g | 300 g |
| DMSO | 600 ml | 800 ml | 160 ml | 80 ml | 600 ml | 600 ml | 600 ml | 200 ml | 300 ml |
| Glycerin | 150 ml | 200 ml | 40 ml | 20 ml | 120 ml | 150 ml | 150 ml | 25 ml | |
| Gel (70/30 DMSO:Water) | 25 g | | | 40 g | 21 g | 100 g | 70 g | 70 g | 25 g | 30 g |
| Gel (85/15 water to MSM) | 125 g | 200 g | | | | | | | |
| *White Camphor | 7 ml | 9 ml | 1.5 ml | 1.25 ml | 7 ml | | 0.5 ml | 1 ml | 3 ml |
| Oil of Wintergreen | 7 ml | 9 ml | | | 2 ml | | | | 0.5 ml |
| Arnica | 4 ml | 5 ml | | | | | | | 0.5 ml |
| Mixed pinenes | 7 ml | 10 ml | | | 2 ml | | | | 1 ml |
| Menthol | 2 g | 1 g | | | | | | | |
| THC:CBD Balm | | | | 10 g | | | | | |
| Spikenard Essential Oil | | | | | | 0.6 ml | | | 0.3 ml |
| ^Klash Terpenes | | | | | 0.5 ml | | | 0.5 ml | |
| Linalool | | | | | | 3.85 ml | 4 ml | | 1 ml |
| α-Pinene | | | | | | 0.5 ml | 0.75 ml | | |
| β-myrcene | | | | | | 0.5 ml | 0.75 ml | | 0.5 ml |
| humulene | | | | | | 0.1 ml | 0.2 ml | | 0.15 ml |
| β-caryophyllene | | | | | | 0.1 ml | 0.2 ml | | 0.5 ml |

*White Camphor: α-Thujene (0.33%), α-Pinene(2.3%), camphene (0.99%), sabinene + β-pinene (13%), 6-methyl-5-heptene-2-one (0.11%), β-Myrcene (9.24%), δ-2-carene (0.1%), α-phellandrene (3.63%), δ-3-carene (0.23%), α-terpinene (5.01%), p-cymene (9%), 1,8-cineole + β-phellandrene + limonene (55.17%), γ-terpinene (0.06%), and α-terpinolene (0.03%)

^Klash Terpenes: Linalool(75%), α-Pinene (11%), β-Myrcene (10.5%), β-Caryophyllene (2%), Humulene (1.5%)

The resulting compositions of these examples are stable lotions that provided fast, effective and long-lasting pain relief when topically applied by several individuals, such as those referenced in Examples 11A-11BA.

Example 8

Example 8 was made by mixing Base Composition B as a source of CBD and terpenoids with other components to yield a topical pain relief composition. Base Composition B was an emulsion manufactured for the inventor in 1-gallon amounts and contained a quantity of hemp CBD oil that provided 10,000 mg of CBD per gallon (0.264% CBD w/v) and terpenoids in a ratio of about 3 parts CBD to about 1-2 parts total terpenoids by weight.

Base Composition B

Base Composition B contained the following in order of prevalence:
Purified water
Capric/Caprylic Triglycerides
Sunflower Seed Oil
Hemp CBD Oil with Terpenes
Moroccan Organic Argan Oil
Emulsifying Wax
Glyceryl Monostearate
*Simmondsia* (jojoba) oil
Butyrospermum Parkii (Shea Butter)
Stearic Acid
Cetyl Alcohol
Glyceryl Distearate
Carbomer.

The ratio of CBD to total terpenes was about 3 parts CBD to about 1-2 parts total terpenoids. The relative amount of each terpenoid as a percentage of total terpenoids was approximately:

| | |
|---|---|
| β-Myrcene | 30% |
| Limonene | 25% |
| β-Caryophyllene | 14% |
| Humulene | 6% |
| Linalool | 4% |
| β-Pinene | 4% |
| α-Pinene | 2.5% |
| α-Bisabolol | 2.5% |
| Terpineol | 2.5% |
| Fenchol | 2.5% |
| Phytol | 1% |
| Nerolidol | 1% |
| Geranic acid | 1% |
| Camphene | 1% |
| Proprietary blend of 7 additional terpenes | 3% |

Base Composition B was mixed with components in the following amounts to yield the composition of Example 8:

| | |
|---|---|
| Base Composition B | 200 g |
| DMSO (99.995%) | 200 ml |
| Gel (70/30 DMSO:Water) | 20 g |
| White camphor | 1 mL |
| Oil of Wintergreen | 5 mL |
| Linalool | 1 mL |

The composition is a stable lotion that provided fast and effect pain relief when topically applied by several individuals, such as those referenced in Examples 11A-11AZ.

Example 9

A liquid pain relief composition was made by combining components in the following amounts:

| | |
|---|---|
| DMSO | 80 mL |
| Glycerin | 20 mL |
| Camphor | 1 mL |
| CBD | 75 mg |
| Klash Terpenes | 0.5 mL |
| Water | 99 mL |

The resulting composition is a stable liquid that provided fast and effect pain relief when topically applied (e.g., by the 58-year-old man and 54-year-old old ultrarunner).

Example 10

The THC-infused muscle relief lotion of Comparative Example D was mixed with components in the following amounts to yield the composition of Example 10:

| | |
|---|---|
| THC-infused muscle relief lotion | 118 ml |
| Base Composition A | 159 g |
| DMSO (99.995%) | 214 ml |
| Glycerin | 53.5 ml |
| DMSO gel (70%) | 42 g |
| Water | 21 ml |
| Camphor | 2 ml |
| Linalool | 2 ml |
| β-Caryophyllene | 0.2 ml |
| Humulene | 0.25 ml |
| β-Myrcene | 0.5 ml |

The resulting composition was a stable lotion that provided fast and effect pain relief when topically applied by several individuals, such as those referenced in Examples 11A-11BA. Some reported even greater relief than CBD-only formulations.

Example A

Any of foregoing Examples is modified to include the following terpene profile:

| | |
|---|---|
| Linalool | 40% |
| β-Myrcene | 20.6% |
| Limonene | 12.7% |
| β-Caryophyllene | 8.1% |
| α-Pinene | 6.9% |
| Humulene | 3.8% |
| β-Pinene | 2.0% |
| α-Bisabolol | 1.3% |
| Terpineol | 1.3% |
| Fenchol | 1.3% |
| Phytol | 0.5% |
| Nerolidol | 0.5% |
| Geranic acid | 0.5% |
| Camphene | 0.5% |

When used with several of Examples 7 and also Example 8, the resulting compositions were highly effective in treating pain.

Example B

Several formulations of Examples 7 and 8 were modified to boost their cannabinoid content. A broad-spectrum CBD oil, which is solid at room temperature, was dissolved in DMSO to a concentration of 10% in some cases and 20% in other cases to yield a CBD-infused DMSO concentrate. This solution was added to the compositions to boost the CBD content provided by the base lotion composition. By this means, the CBD content was increased by 2-10 times. In some formulations, the CBD concentration was about 300 mg per fluid ounce. When applied to a region of pain, the compositions worked well, sometimes better than the original formulations containing less CBD.

Example C

Several formulations of Examples 7 and 8 were modified to boost and modify their cannabinoid content. A broad spectrum, hemp-derived delta-8 THC oil, which is solid at room temperature, was dissolved in DMSO to a concentration of 10% to yield a hemp-derived THC-infused DMSO concentrate. This solution was added to the compositions to add THC to provide a composition containing both THC and CBD. In some formulations, the THC concentration was about 300 mg per fluid ounce. When applied to a region of pain, these compositions worked well, typically better than the original formulations containing only CBD. This suggests that combining THC and CBD can provide synergistic pain relief that cannot be obtained using each individually.

Example D

Several formulations of Examples 7 and 8 were modified to boost and modify their cannabinoid content. The CBD-infused DMSO concentrate of Example B and the hemp-derived THC infused DMSO concentrate of Example C were both added to provide approximately 150 mg of CBD per fluid ounce and approximately 150 mg of THC per fluid ounce, for a total of 300 mg of cannabinoids per fluid ounce. These compositions were perceived to work better than other compositions. Again, this suggests that combining THC and CBD provide synergistic pain relief that cannot be obtained using each individually.

Examples 11A-11BG (Experimental Uses)

Persons were given one or more compositions of Examples 1-10 and Examples A-D and asked to apply the composition to the affected area. They were instructed to ensure the skin is clean and dry before application.

| Example | Person-Age | Ailment-Result |
|---|---|---|
| 11A | Woman-36 | Chronic hamstring pain; applied to affected area; reduced or eliminated pain |
| 11B | Man-48 | Golfer with sore forearm; applied to affected area; reduced or eliminated pain |
| 11C | Man-40 | Golfer with sore shoulder that prevented normal swing; applied to affected area; reduced or eliminated pain and restored normal swing |
| 11D | Man-50 | Tennis elbow; applied to affected are; total relief and restored normal swing |
| 11E | Woman-45 | Headache-applied to forehead and obtained total relief |
| 11F | Man-58 | Painful knee from patellar tendon surgery (applied to knee; pain reduced from 5 to 1); painful foot following ankle surgery (applied to foot; pain reduced from 5 to 0 after overnight application) |
| 11G | Man-54 | Runner applied to legs before and after running; almost total relief |
| 11H | Woman-67 | Back pain; applied to affected area; reduced pain from 5 to 1 |
| 11I | Various Ultrarunners | Muscle and joint pain; applied to affected areas before and after runs to prevent and relief pain |
| 11J | Man-50 | Ultrarunner ran 100 miles, applied to affected areas after race and next day able to run 20 miles uphill with little pain; never recovered so quickly before |
| 11K | Man-54 | Applied to legs and feet before running up and down Pfeifferhorn (11,350 ft summit); felt no pain during hike; when pain later arose applied Example 2 over Example 1 for extra relief |
| 11L | Man-56 | Cancer patient applied to thigh and back; partial relief |
| 11M | Woman-27 | Massage therapist with sore wrist with cyst; applied to cyst regularly, did not require surgery; cyst pain and size reduced |
| 11N | Woman-40 | Secretary developed neck pain while sitting for hours in front of computer; applied to neck; total pain relief in less than 2 minutes ("I don't know how it works, it just does") |
| 11O | Man-32 | Sore shoulder; applied to shoulder; pain reduced from 5 to 1 within 5 minutes |
| 11P | Woman-23 | Yoga instructor with pinched nerve in back; applied to affected area; obtained almost total relief in <1 minute |
| 11Q | Man-55 | Drummer with chronically sore wrists applied to wrists and ankles and obtained total relief; less effective for back |
| 11R | Man-35 | Soccer goalkeeper applied to sore wrist; total relief |
| 11S | Woman-40 | Massage therapist applied to sore necks of herself and 18-year-old daughter; both felt pain vanish in minutes |
| 11T | Man-60 | Has Parkinson's with painful wrist joints; applied to affected areas; obtained high level of relief; uses daily to manage pain |
| 11U | Man-37 | Hurt back lifting heavy object; hurt two days later and applied to back; relieved the pain |
| 11V | Woman-41 | Wife of man in 11U applied to bursitis and obtained total relief |
| 11W | Man-58 | Recurring pain in thumb from typing at computer-2-3 applications to thumb caused pain to subside |
| 11X | Man-65 | Applied to sore knee after hiking and pain subsided; applied to post-surgical shoulder for total relief |
| 11Y | Man-18 | Broken back and laid up for 8 month-applied to back several times and reduced pain by at least ⅔ |
| 11Z | Man-48 | Chronically painful hands; applied to hand and pain resolved in minutes |
| 11AA | Man-52 | Ultrarunner with back, hip and neck pain previously tried CBD products but obtained no relief; applied composition twice daily and runs virtually pain free; when driving from cabin for 2.5 hours, experienced intense arthritic pain in thumb and index finger, which locked up, requiring manual straightening with other hand (see quote below); applied product to affected areas and obtained total relief and restoration of movement |
| 11AB | Man-72 | Recovered stroke victim with foot pain; applied to feet and obtains almost total relief; reduced prescription pain meds by half |
| 11AC | Woman-65 | Neighbor of man in 11AB applied to sore thumb and neck and obtained total relief, unlike other CBD products |
| 11AD | Various | Friends of Woman in 11AC who drive boats applied to hands and arms for instant relief |

-continued

| Example | Person-Age | Ailment-Result |
|---|---|---|
| 11AE | Man-71 | Retired army colonel has chronic pain and used other CBD products; this composition worked far better than all others |
| 11AF | Man-66 | Dentist with chronic shoulder pain almost had to retire; applied to shoulder; product permitted him to resume working 10-hour days virtually pain-free |
| 11AG | Woman-68 | Has multiple sclerosis and has sore muscles and joints; tried other CBD products but only this one worked |
| 11AH | Man-48 | Has chronic arthritis in back and joints and is hunched over much of the time; applied by massage therapist and recovered 90% of normal movement and posture |
| 11AI | Man-42 | Plantar fasciitis and wakes up hardly able to walk; applied to bottom of feet each night before bed and woke up pain free; after 6 months pain permanently went away |
| 11AJ | Woman-67 | Plantar fasciitis; applied to feet; obtained almost total relief |
| 11AK | Man-45 | Very painful and stiff shoulders; applied to shoulders by massage therapist and recovered range of motion |
| 11AL | Man-84 | Age-related pain; applied to affected areas to effectively relieve pain |
| 11AM | Woman-87 | Sore neck; applied to neck as needed for high level of relief |
| 11AN | Woman-30 | Professional skier with muscular and joint pain; applied to affected areas for high level of relief |
| 11AO | Woman-62 | Receptionist with chronic pain in thumb joint; provided total relief when applied to joint regularly; stopped using for 3 weeks and pain returned; next application relieved pain as before |
| 11AP | Woman-30 | Effective for direct application to affected area to treat recurring back pain |
| 11AQ | Man-81 | Walks with a cane; applied to affected areas; effective for back pain, leg pain, ankle, foot pain, and arthritic pain |
| 11AR | Man-48 | Elbow Pain from celiac disease; applied to affected area; provided 80-90% reduction in pain |
| 11AS | Man-50 | Recovering from deltoid muscle surgery-applied to deltoid to manage pain post-surgery (60-80% reduction in pain) |
| 11AT | Man-55 | Developed painful sciatica and could barely walk; applied to buttocks and back and was able to hike 8 miles |
| 11AU | Woman-84 | Had a locked finger and sore neck; applied to neck using hand and said it didn't provide total relief; inadvertently unlocked finger of applying hand |
| 11AV | Man-43 | Same man in 11AI had intense shoulder pain under the scapula; applied to affected area and obtained total relief |
| 11AW | Man-58 | Building contractor had hands so painful he could no longer hold tools and was going to quit; applies to hands daily to obtain relief sufficient to continue working with little to no pain. |
| 11AX | Man-60 | Same man in 11F had sore IT band a few days after strenuous hike; applied one time to affected area along outside of thigh before bed; pain completely gone next day |
| 11AY | Man-45 | Had sore forearms from heavy lifting during home remodel; applied product to affected areas; obtained almost total relief |
| 11AZ | Woman-47 | Pain in tendon connecting thigh to pelvis following workouts; applied to affected area; provided total relief after 2 applications |
| 11BA | Man-41 | Body builder suffering from inner tendonitis at the elbow where the bicep muscle attaches to the ulna regularly applied to affected area to relieve pain and promote healing during physical therapy; cancelled surgery |
| 11BB | Man-70 | "I've battled fibromyalgia, degenerate disc, bone spurs, old back fractures, arthritis, now a broken leg 2 months ago. I've [sic] very used to physical pain daily. It absolutely still blows my mind how well this works!" |
| 11BC | Man-60 | The inventor obtained permanent relief for intense neck-trapezius-shoulder pain after just a few days of application; first application reduced pain from 7 to 0 within minutes; applies about once a month for maintenance if neck stiffens for total relief. |
| 11BD | Man-38 | Had sciatica; applied to lower back and pain eliminated. |
| 11BE | Man-35 | Had sciatica; applied to lower back and pain eliminated. |
| 11BF | Man-30 | Overweight man with back pain; very effective to eliminate pain when needed. |

-continued

| Example | Person-Age | Ailment-Result |
|---|---|---|
| 11BG | Man-40 | "Salveation is instant relief when I've hurt my back. I also use it preemptively if I know I am going to be doing an activity that is going to strain my back. I use it primarily on my lower back on the area around my L1 & L2 discs, as they both have degeneration issues. The salve will take me from a 7 (on a scale of 1-10, 10 the worst) down to a 3 in short order. I gladly endorse the salve to anyone who has moderate to severe back pain." |

Ultrarunner in Example 11AA wrote the following: "I didn't want to sound over the top in the last review I sent you but I need to tell you the other two things that Salvation has done for me: (1) I have bad arthritis in my thumb and index finger on my left hand. Yesterday while driving home from our cabin they would lock up in a half first position and I would have to straighten them back out with my other hand. This happened at least a dozen times in the 2½ hour drive. As soon as I got home, I put Salvation on them and the pain and cramps went away. I'm sure they will return in the future but now I have a remedy. (2) I have suffered with plantar fasciitis for over 30 years. Two surgeries and several shots later there was no hope. I started running when I was 46 and that and 0 drop Altras seemed to be my cure. Due to my neck issues I quit running for six months and now the PF has returned with a vengeance. I work 10 hour days in steel toe boots standing on concrete and by the end of my shift I could hardly walk. I started pre treating with Salvation and I am mostly pain free. This stuff really has been my Salvation!"

The disclosed compositions have been found to be especially useful in treating chronic pain, including idiopathic pain with no specific pathology or known cause, and in older (e.g., 50 or above) or infirm persons, who have tried conventional pain remedies with little or no relief. The product has been described as miraculous by many. Because it does not feel like a counterirritant, it does not provide the usual cooling and/or heating sensation of such products. Rather, it seems to work to reduce or eliminate pain through a different mechanism. Some have proclaimed "it just works".

Comparative Study

A comparative study was performed comparing a preferred composition made according with a representative composition in US Publication No. 2016/0256411 (Aung-Din), which discloses a method of administering a cannabinoid to the back of the neck region at the hairline (BON-ATH) in order to deliver the cannabinoid to the brain stem and/or trigeminal nerves to provide pain relief to a different part or region of the body. This is called topical regional neuro-affective therapy ("TRNA therapy").

Example 3 of Aung-Din is the only working example of a composition which contains DMSO and CBD and is therefore a valid representative composition of Aung-Din. Following is a quotation of Example 3:

Example 3

Oil-Based CBD

A 30 g topical formulation of CBD is prepared by incorporating CBD oil, Dimethyl sulfoxide 3 ml and enough base for total quantity of 30 grams. The CBD is incorporated in a concentration sufficient to yield an end product having a CBD concentration of 0.75%, 1%, 1.5%, 2% and 3%. The topical formulation is in the form of a cream. The oil-based CBD includes CBD oil commercially available from CannaVest. A unit dose of the topical CBD cream is from about 0.5 to about 1 g, with respect to formulations having a CBD concentration from 1.5%-3%. After initial application, the topical CBD formulation can be applied to the back of the neck of the human patient once a day, twice a day, three times a day, or four times a day depending on the condition to be treated and its severity.

Example 3 therefore provides the following information about the composition:
3 ml of DMSO;
CBD oil incorporated in a concentration sufficient to yield an end product having a CBD concentration of 0.75%, 1%, 1.5%, 2%, or 3% CBD; and
enough base for a total of 30 grams of topical formulation.

Aung-Din does not identify what is in the "base" used in Example 3. Paragraph [0180] of Aung-Din is the only place where a definition of a "base" is provided: "Carrier materials suitable for use in the instant compositions include those well-known for use in the cosmetic and medical arts as bases for ointments, lotions, salves, aerosols, suppositories and the like." Thus, ointments, lotions, and salves used in the cosmetic and medical arts are all suitable "bases" for reproducing Example 3 of Aung-Din.

The CBD lotion or cream identified as "Base Composition A" and used in Examples 7A-7R above was determined to a suitable "base". It is sold commercially by Koodegras (CBD store), located in Salt Lake City, Utah. A gallon of Base Composition A was purchased directly from the manufacturer and used to make the compositions for the Comparative Study.

As set forth above, Base Composition A contained the following components:
Purified water
Capric/Caprillic Triglycerides
Sunflower Seed Oil
Hemp CBD Oil with Terpenes
Moroccan Organic Argan Oil
Emulsifying Wax
Glyceryl Monostearate
*Simmondsia* (jojoba) oil
Butyrospermum Parkii (Shea Butter)
Stearic Acid
Cetyl Alcohol
Glyceryl Distearate
Carbomer.

Base Composition A contained 10,000 mg of CBD per gallon (0.26% by weight) and terpenes, which are identified in paragraph [0105] of the Application as being linalool (75%), α-pinene (11%), β-myrcene (10.5%), β-caryophyllene (2%), and humulene (1.5%). The weight ratio of CBD was about 3 parts CBD to about 1 to 2 parts of total terpenes.

A composition representative of Example 3 of Aung-Din ("Aung-Din Composition") was made by mixing CBD oil, DMSO, and Base Composition A in the same relative amounts set forth in paragraph [0220] of Aung-Din to yield a composition containing 1.5% by weight of CBD:

| CBD Oil | q.s to 1.5 wt % |
|---|---|
| DMSO | 30 ml |
| Base Composition A | q.s. to 300 g |

A representative composition of the disclosure ("Inventive composition") was made by mixing together the following components to yield a composition containing CBD and other hemp-derived cannabinoids totaling 0.75% by weight:

| Base Composition A | 932 g |
|---|---|
| DMSO | 932 g |
| Glycerin | 37.3 g |
| Water | 93.2 g |
| Aqueous gel (2% carbomer) | 90 g |
| CBD and hemp-derived cannabinoids | 13.5 g |
| Terpenes | 7 g |
| Total | 2,105 g |

The Aung-Din Composition contained approximately twice the concentration of CBD as the combined concentration of CBD and other hemp-derived cannabinoids in the Inventive Composition and approximately one-fourth the concentration of DMSO.

The participants of the comparative study were provided with quantities of the Aung-Din Composition and the Inventive Composition and asked to define their pain on a scale of 1 to 10 before and 15-30 minutes after using each composition. The recommended amount to be applied was a nickel-sized amount.

An 83 year old man suffering from intense chronic lower back pain, with an initial pain level of 10, applied the Inventive Composition to the lower back at the location of the pain and obtained a high level of relief, reducing the pain level from 10 to 2. When the pain returned, the man applied the Aung-Din Composition to the lower back and obtained no discernable relief. Thereafter, the man applied the Inventive Composition to the lower back at the location of the pain when the pain level was 9 and again obtained a high level of relief, reducing the pain level from 9 to 1.

A 55 year old woman suffering from intense neck pain from working long hours typing at a computer, with an initial pain level of 8, applied the Inventive Composition to the neck at the location of the pain and obtained a high level of relief, reducing the pain level from 8 to 2. When the pain returned, the woman applied the Aung-Din Composition to the neck and obtained no discernable relief (initial and final pain levels were 8). Thereafter, the woman applied the Inventive Composition to the neck at the location of the pain when the pain level was 8 and again obtained a high level of relief, reducing the pain level from 8 to 2.

A 30 year old man suffering from periodic lower back pain, with an initial pain level of 5, applied the Inventive Composition to the lower back at the location of the pain and obtained significant pain relief, reducing the pain level from 5 to 2. When the pain returned, the man applied the Aung-Din Composition to the lower back, which only slightly reduced the pain level from 5 to 4. Thereafter, the man applied the Inventive Composition to the lower back at the location of the pain when the pain level was 5 and again obtained significant pain relief, reducing the pain level from 5 to 2.

A 49 year old man suffering from celiac disease commonly experiences pain in the elbow and fingers. When the pain was at an initial pain level of 5, the man applied the Inventive Composition at the location of the pain and obtained total relief, with a pain level of 0. When the pain returned, the man applied the Aung-Din Composition at the location of the pain and obtained no discernable relief (initial and final pain levels were 5). Thereafter, the man applied the Inventive Composition at the location of the pain when the pain level was 5 and again obtained a high level of relief, reducing the pain level from 5 to 1.

A 57 year old man suffering from pain in the wrists, hands and feet, with an initial pain level of 7, applied the Inventive Composition at the location of the pain and obtained significant relief, with a resulting pain level of 4. When the pain returned, the man applied the Aung-Din Composition at the location of the pain, which only slightly reduced the pain level from 7 to 6. Thereafter, the man applied the Inventive Composition at the location of the pain when the pain level was 6 and again obtained a high level of relief, reducing the pain level from 6 to 2.

A 49 year old man suffering from pain in the thumb joints of both hands, with an initial pain level of 6, applied the Inventive Composition at the location of the pain and obtained total relief, reducing the pain level from 6 to 0. When the pain returned to a pain level of 5, the man applied the Aung-Din Composition at the location of the pain and obtained no discernable relief (beginning and final pain levels were 5). Thereafter, the man applied the Inventive Composition at the location of the pain when the pain level was 5 and again obtained total relief, reducing the pain level from 5 to 0.

A 60 year old man suffering from neck, knee, and foot pain of varying degrees, applied the Inventive Composition to the neck and obtained almost total relief, reducing the pain level from 7 to 1. When the pain returned to a pain level of 4, the man applied the Aung-Din Composition to the location of the pain and obtained no discernable relief (beginning and final pain levels were 4). Thereafter, the man applied the Inventive Composition to the neck when the pain level was 5 and again obtained total relief, reducing the pain level from 5 to 0.

The 60 year old man applied the Inventive Composition to a foot experiencing neuropathic pain at a pain level of 5 and obtained almost total relief to a pain level of 1 after overnight application. A similar overnight application of the Aung-Din Composition to the same foot when the neuropathic pain returned to a pain level of 4 resulted in no discernable relief. The man routinely applies the Inventive Composition to the foot when sore and obtains a high level of relief.

A 49 year old woman who recently had neck surgery, with an initial pain level of 8, applied the Inventive Composition to the neck and obtain modest pain reduction to a pain level of 5 or 6. When the pain returned to a pain level of 8, the woman applied the Aung-Din Composition at the location of the pain and was only able to reduce the pain level from 8 to 7. Thereafter, the woman applied the Inventive Composition at the location of the pain when the pain level was 8 and obtained modest relief down to a pain level of 6.

A 43 year old man who had recently competed in an ultramarathon had lower back pain at an initial pain level of 4. The Aung-Din Composition was applied at the location of the pain and provided a modest amount of relief from 4 to 3. Thereafter, when the pain returned to a pain level of 4, the Inventive Composition was applied at the location of the pain and reduced the pain from a pain level of 4 to 1.

A 29 year woman suffering from pain in the wrists, lower back, and neck with an initial pain level of 9, applied the Inventive Composition at the location of the pain and obtained significant relief, reducing the pain level from 9 to 3. When the pain returned to a pain level of 9, the woman applied the Aung-Din Composition at the same location and obtained slight relief from 9 to 7. Thereafter, the woman applied the Inventive Composition at the location of the pain when the pain level was 9 and again experienced significant relief from a pain level of 9 to 4.

A 52 year woman suffering from pain in the neck, mid back, and knees with an initial pain level of 4, applied the Inventive Composition at the location of the pain and obtained total relief, reducing the pain level from 4 to 0. When the pain returned to a pain level of 3, the woman applied the Aung-Din Composition at the same location and obtained no discernable relief. Thereafter, the woman applied the Inventive Composition at the location of the pain when the pain level was 4 and again experienced total relief from a pain level of 4 to 0.

The Comparative Study shows that the Inventive Composition was significantly more effective than the Aung-Din Composition in providing localized pain relief, i.e., at the location where applied.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A composition for topical pain relief, comprising:
   a cannabinoid component;
   a terpenoid component;
   25% to 75% by weight of dimethyl sulfoxide (DMSO);
   a fatty component; and
   a compatibilizer,
   wherein the ratio of DSMO to compatibilizer is greater than 1:1 by weight.

2. The composition of claim 1, wherein the cannabinoid component is selected from the group consisting of tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), tetrahydrocannabivarin (THCV), cannabidivarin (CBDV), cannabichromevarin (CBCV), cannabigerovarin (CBGV), delta-8-tetrahydrocannabinol, delta-9-tetrahydrocannabinol (Dronabinol), cannabigerol monomethyl ether (CBGM), nabilone, and combinations thereof.

3. The composition of claim 1, wherein the terpenoid component is selected from the group consisting of α-pinene, β-pinene, camphene, β-myrcene, humulene, α-bisabolol, β-caryophyllene, linalool, camphor, limonene, ocimene, α-phellandrene, 1,8-ceneole, eucalyptol, γ-terpinene, terpineol, fenchol, phytol, nerolidol, geranyl acetate, sabinene, p-cymene, β-phellandrene, valencene, borneol, isoborneol, geraniol, δ-3-carene, terpinolene, and combinations thereon.

4. The composition of claim 1, wherein the ratio (w/w) of total terpenoids to total cannabinoids is in a range of about 1:10 to about 5:1.

5. The composition of claim 1, wherein the composition comprises at least one component selected from the group consisting of aspirin (acetyl salicylic acid), non-steroidal anti-inflammatory drugs (NSAIDs), methyl salicylate, menthol, *arnica* oil, spikenard, peppermint oil, oil of wintergreen, mixed pine terpenes, and pure gum spirits of turpentine.

6. The composition of claim 1, wherein the cannabinoid component comprises at least one of cannabidiol (CBD) or tetrahydrocannabinol (THC) and the terpenoid component comprises at least three of linalool, α-pinene, β-myrcene, β-caryophyllene, or humulene and/or at least five of β-myrcene, limonene, β-caryophyllene, humulene, linalool, β-pinene, α-pinene, α-bisabolol, terpineol, fenchol, phytol, nerolidol, geranyl acetate, or camphene.

7. The composition of claim 1, wherein the composition comprises 25% to 70% by weight of the DMSO.

8. The composition of claim 1, wherein the compatibilizer is selected from the group consisting of alcohols, polyols, thiols, carboxylic acids, carboxylates, polycarboxylates, esters, amides, ketones, aldehydes, ethers, sulfonates, phosphonates, amines, and combinations thereof.

9. The composition of claim 8, wherein the compatibilizer comprises one or more polyols selected from the group consisting of glycerin, propylene glycol, 1,3-propanediol, 1,3-butanediol, sorbitol, xylitol, and polyethylene glycol.

10. The composition of claim 1, wherein the fatty component comprises one or more components selected from the group consisting of fatty acids, caproic acid, capric acid, caprillic acid, lauric acid, medium chain fatty acids, stearic acid, isostearic acid, octanoic acid, oleic acid, linoleic acid, linolenic acid, esters of fatty acids, mono-, di- and/or triglycerides of fatty acids, olive oil, sunflower seed oil, coconut oil, cocoa butter, jojoba oil, almond oil, pine needle oil, shea butter, argan oil, nigella *sativa* oil, beeswax, and flaxseed oil.

11. The composition of claim 1, further comprising water and wherein the composition is an emulsion.

12. The composition of claim 1, wherein the composition is a cream, lotion, gel, suspension, ointment, or liquid.

13. The composition of claim 1, wherein the composition is a muscle rub, massage oil, spray, or roll-on.

14. A kit comprising the composition of claim 1 in a container and a plurality of bandages, patches, or other barrier layers.

15. An article of manufacture comprising the composition of claim 1 and a bandage, patch, or other barrier layer on which the composition is disposed.

16. A composition for topical pain relief, comprising:
   0.05-10% by combined weight of one or more cannabinoids selected from the group consisting of tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), tetrahydrocannabivarin (THCV), cannabidivarin (CBDV), cannabichromevarin (CBCV), cannabigerovarin (CBGV), delta-8-tetrahydrocannabinol, delta-9-tetrahydrocannabinol (Dronabinol), cannabigerol monomethyl ether (CBGM), nabilone, and combinations thereof;

one or more terpenes;

25% to 70% by weight of DMSO;

a compatibilizer;

*arnica*; and a fatty component comprising at least one of capric/caprylic triglycerides, sunflower seed oil, argan oil, emulsifying wax, glyceryl monostearate, jojoba oil, shea butter, almond oil, coconut oil, olive oil, nigella *sativa* oil, black seed (cumin) oil, lauric acid, medium chain fatty acids, stearic acid, isostearic acid, mono-, di- or triglyceride of fatty acids, coconut oil, cocoa butter, beeswax, or flaxseed oil.

17. The composition of claim 16, wherein the terpenes comprise at least two of linalool, α-pinene, β-myrcene, β-caryophyllene, or humulene.

18. The composition of claim 16, wherein the composition is a spray or roll-on.

19. A composition for targeted topical pain relief, comprising:

0.05% to 10% by combined weight of at least one cannabinoid selected from the group consisting of tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), tetrahydrocannabivarin (THCV), cannabidivarin (CBDV), cannabichromevarin (CBCV), cannabigerovarin (CBGV), delta-8-tetrahydrocannabinol, delta-9-tetrahydrocannabinol (Dronabinol), cannabigerol monomethyl ether (CBGM), nabilone, and combinations thereof;

0.002% to about 4% by combined weight of at least one terpene selected from the group consisting of α-pinene, β-pinene, camphene, β-myrcene, humulene, α-bisabolol, β-caryophyllene, linalool, camphor, limonene, ocimene, α-phellandrene, 1,8-ceneole, eucalyptol, γ-terpinene, terpineol, fenchol, phytol, nerolidol, geranyl acetate, sabinene, p-cymene, β-phellandrene, valencene, borneol, isoborneol, geraniol, δ-3-carene, terpinolene, and combinations thereof;

25% to 70% by weight of dimethyl sulfoxide (DMSO);

a fatty component; and a compatibilizer.

20. The composition of claim 19, further comprising water, and wherein the composition is an emulsion.

* * * * *